(12) United States Patent
Deck

(10) Patent No.: US 11,426,248 B2
(45) Date of Patent: Aug. 30, 2022

(54) FUNCTIONAL MEDICAL PACKAGE AND MEDICAL DEVICE FOR INSERTING AT LEAST ONE SUBSYSTEM INTO A HOST

(71) Applicant: ROCHE DIABETES CARE, INC., Indianapolis, IN (US)

(72) Inventor: Frank Deck, Niederkirchen (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 959 days.

(21) Appl. No.: 16/047,449

(22) Filed: Jul. 27, 2018

(65) Prior Publication Data

US 2018/0344422 A1    Dec. 6, 2018

Related U.S. Application Data

(63) Continuation of application No. PCT/EP2017/051794, filed on Jan. 27, 2017.

(30) Foreign Application Priority Data

Jan. 29, 2016    (EP) .................................... 16153330

(51) Int. Cl.
*A61B 50/30* (2016.01)
*A61B 5/15* (2006.01)
(Continued)

(52) U.S. Cl.
CPC ........ *A61B 50/30* (2016.02); *A61B 5/150305* (2013.01); *A61M 5/002* (2013.01);
(Continued)

(58) Field of Classification Search
None
See application file for complete search history.

(56) References Cited

U.S. PATENT DOCUMENTS 5,413,690 A    5/1995 Kost et al.
5,762,770 A    6/1998 Pritchard et al.
(Continued)

FOREIGN PATENT DOCUMENTS

RU    2 159 085 C1    11/2000
RU    114 413 U1    3/2012
(Continued)

OTHER PUBLICATIONS

International Search Report and Written Opinion of the International Searching Authority, PCT/EP2017/051794, dated Mar. 24, 2017, 9 pages.
(Continued)

*Primary Examiner* — Jay B Shah
(74) *Attorney, Agent, or Firm* — Bose McKinney & Evans LLP

(57) ABSTRACT

A functional medical package is disclosed having a disposable package and a sterile container removably received inside the disposable package. A subsystem is received in the sterile container and is configured to be at least partially inserted into a host. The sterile container has an insertion exit opening for the subsystem and a liner closes the insertion exit opening. The liner is attached to the disposable package and automatically peels off the insertion exit opening when the sterile container is removed from the disposable package. Also disclosed are a method of manufacturing the medical package and a method of using the medical package with an inserter.

13 Claims, 11 Drawing Sheets

(51) Int. Cl.
*A61M 5/00* (2006.01)
*B65B 55/04* (2006.01)
*A61B 50/00* (2016.01)
*A61B 5/1473* (2006.01)

(52) U.S. Cl.
CPC ............ *B65B 55/04* (2013.01); *A61B 5/1411* (2013.01); *A61B 5/1473* (2013.01); *A61B 5/15003* (2013.01); *A61B 2050/0065* (2016.02); *A61B 2562/242* (2013.01); *A61M 2207/00* (2013.01)

(56) References Cited

U.S. PATENT DOCUMENTS

| | | | |
|---|---|---|---|
| 5,798,031 | A | 8/1998 | Charlton et al. |
| 6,129,823 | A | 10/2000 | Hughes et al. |
| 6,360,888 | B1 | 3/2002 | McIvor et al. |
| 9,101,305 | B2 | 8/2015 | Larson et al. |
| 9,616,165 | B2 | 4/2017 | Larson et al. |
| 2005/0013731 | A1 | 1/2005 | Burke et al. |
| 2008/0242962 | A1 | 10/2008 | Roesicke et al. |
| 2008/0319416 | A1 | 12/2008 | Yodfat et al. |
| 2009/0163874 | A1 | 6/2009 | Krag et al. |
| 2016/0193427 | A1* | 7/2016 | Limaye ................. A61M 5/321 206/365 |

FOREIGN PATENT DOCUMENTS

WO  WO 2013/178499 A1  12/2013
WO  WO 2015/122964 A1  8/2015

OTHER PUBLICATIONS

International Preliminary Report on Patentability and Written Opinion of the International Searching Authority, PCT/EP2017/051794, dated Jul. 31, 2018, 6 pages.

* cited by examiner

FUNCTIONAL MEDICAL PACKAGE AND MEDICAL DEVICE FOR INSERTING AT LEAST ONE SUBSYSTEM INTO A HOST

RELATED APPLICATIONS

This application is a continuation of PCT/EP2017/051794, filed Jan. 27, 2017, which claims priority to EP 16 153 330.2, filed Jan. 29, 2016, the entire disclosures of both of which are hereby incorporated herein by reference.

BACKGROUND

This disclosure relates to functional medical packages and medical devices for inserting at least one subsystem into a host. This disclosure may both be applied in the field of home care and in the field of professional care, such as in hospitals. Other applications are feasible. The devices and methods according to the present disclosure may mainly be used for long-term monitoring of an analyte concentration in a body fluid, such as for long-term monitoring of a blood glucose level or of the concentration of one or more other types of analytes in a body fluid.

Monitoring certain body functions, more particularly monitoring one or more concentrations of certain analytes, plays an important role in the prevention and treatment of various diseases. Without restricting further possible applications, this disclosure will be described in the following text with reference to blood-glucose monitoring. However, additionally or alternatively, this disclosure can also be applied to other types of analytes.

Blood glucose monitoring, besides by using optical measurements, specifically may be performed by using electrochemical biosensors. Examples of electrochemical biosensors for measuring glucose, specifically in blood or other body fluids, are known from U.S. Pat. Nos. 5,413,690 A, 5,762,770 A, 5,798,031 A, 6,129,823 A or US 2005/0013731 A1.

In addition to so-called spot measurements, in which a sample of a bodily fluid is taken from a user in a targeted fashion and examined with respect to the analyte concentration, continuous measurements are increasingly becoming established. Thus, in the recent past, continuous measuring of glucose in the interstitial tissue (also referred to as continuous monitoring, CM) for example has been established as another important method for managing, monitoring and controlling a diabetes state.

In the process, the active sensor region is applied directly to the measurement site, which is generally arranged in the interstitial tissue, and, for example, converts glucose into electrical charge by using an enzyme (e.g., glucose oxidase, GOD), which charge is related to the glucose concentration and can be used as a measurement variable. Examples of such transcutaneous measurement systems are described in U.S. Pat. No. 6,360,888 B1 or in US 2008/0242962 A1.

Hence, current continuous monitoring systems typically are transcutaneous systems or subcutaneous systems, wherein both expressions, in the following, will be used equivalently. This means that the actual sensor or at least a measuring portion of the sensor is arranged under the skin of the user. However, an evaluation and control part of the system (also referred to as a patch) is generally situated outside of the body of the user, outside of the human or animal body. In the process, the sensor is generally applied using an insertion instrument, which is likewise described in U.S. Pat. No. 6,360,888 B1 in an exemplary fashion. Other types of insertion instruments are also known.

The sensor typically comprises a substrate, such as a flat substrate, onto which an electrically conductive pattern of electrodes, conductive traces and contact pads may be applied. In use, the conductive traces typically are isolated by using one or more electrically insulating materials. The electrically insulating material typically further also acts as a protection against humidity and other detrimental substances and, as an example, may comprise one or more cover layers such as resists.

As outlined above, in transcutaneous systems, a control part is typically required, often also referred to as an electronics unit or a transmitter, which may be located outside the body tissue and which has to be in communication with the sensor. Typically, this communication is established by providing at least one electrical contact between the sensor and the control part, which may be a permanent electrical contact or a releasable electrical contact.

WO 2013/178499 A1 discloses a sensor cartridge comprising a sterile capsule. The sensor cartridge further comprises a sensor within the sterile capsule. The sensor cartridge further comprises a sensor connector connected to the sensor in an initial position. The sensor cartridge further comprises an insertion needle for inserting the sensor into a subject. The insertion needle is within the sterile capsule. The sensor cartridge further comprises a sensor mounting unit for receiving the sensor connector at a mounted position. The sensor mounting unit comprises an adhesive surface for attaching to an exterior surface of the subject. The sensor cartridge further comprises an insertion mechanism operable for actuating the insertion needle and moving the sensor connector from the initial position to the mounted position.

US 2009/0163874 A1 discloses an assembly comprising a skin-mountable device with an adhesive mounting surface, the device being arranged in a packaging comprising an opening with a surrounding portion and being closed with a seal member releasably attached to the surrounding portion, thereby providing a closed space for the device. The seal member has an inner surface releasably attached to the adhesive, the seal member being penetratable by a sterilizing gas. The inner surface is partially coated with a material allowing the seal member to be peeled from the adhesive, yet allows the sterilizing gas to penetrate the seal member. In this way a seal member is provided which to a high degree has two desirable properties: being gas penetratable yet allows the seal member to be peeled from the adhesive surface.

WO 2015/122964 A1 discloses a system and a method for packaging and sterilizing analyte sensors. The packaging system provides a structure for securing the analyte sensors in a fixed position and fixed orientation within the package.

U.S. Pat. No. 9,101,305 B2 discloses a manufacturing process for a glucose sensor product. The process maintains the sterility of the glucose sensor while allowing gaseous manufacturing by-products to be vented from the inside of the glucose sensor package. The method begins by placing a glucose sensor assembly into a plastic package tray having a sealing surface surrounding an opening. The method continues by covering the opening with a microbial barrier material such that the microbial barrier material overlies the sealing surface, forming a seal between the sealing surface and the microbial barrier material, resulting in a sealed package tray containing the glucose sensor assembly, and sterilizing the glucose sensor assembly inside the sealed package tray. The microbial barrier material maintains sterility of the glucose sensor assembly while allowing volatile by-products outgassed from the glucose sensor assembly and the plastic package tray to pass therethrough.

Despite the advantages implied by the above-mentioned devices and methods, a plurality of problems and technical challenges remain. Thus, sterilization of the devices or parts thereof remains an issue. Typically, as an example, in assemblies comprising one or more electrochemical sensors, the census require electron beam sterilization, since the chemical component of the electrochemical sensors is sensitive against other sterilization means such as chemical sterilization. Other components of the assemblies, however, typically are sterilized via gas sterilization such as by using ethylene oxide. Consequently, many assemblies known in the art, in practice, require a separate handling and a separate sterilization of the components. As an example, the sensor inside the assembly may be packaged separately, a sterile capsule may be used for the sensor, or separate packages for the components may be used. These means and methods, however, are fairly complicated and render the assembly process as well as the sterilization process rather time-consuming and inefficient.

SUMMARY

This disclosure provides a functional medical package, a medical device for inserting at least one subsystem into a host, a method of manufacturing the functional medical package as well as a method for picking up a subsystem configured for being at least partially inserted into a host by an inserter which at least partially address the above-mentioned challenges and shortcomings of devices and methods of this kind. Specifically, a functional medical package is taught, which reduces a sterilization such as an electron beam sterilization only or at least to a large extent to a subsystem and which enables a simple handling.

As used in the following, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B," "A comprises B" and "A includes B" may both refer to a situation in which, besides B, no other element is present in A (i.e., a situation in which A solely and exclusively consists of B) and to a situation in which, besides B, one or more further elements are present in entity A, such as element C, elements C and D or even further elements.

Further, it shall be noted that the terms, when used herein, "at least one," "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, notwithstanding the fact that the respective feature or element may be present once or more than once. In the same connection, regardless of whether the phrases "one or more" or "at least one" precede an element or feature presented in this disclosure or claims, it shall be understood that such element or features shall not receive a singular interpretation unless it is made explicit herein. By way of non-limiting example, the terms "sterile container," "subsystem," "liner," to name just a few, should be interpreted when appearing in this disclosure and claims to mean "at least one" or "one or more" regardless of whether they are introduced with the expressions "at least one" or "one or more." All other terms used herein should be similarly interpreted unless it is made explicit that a singular interpretation is intended.

Further, as used in the following, the terms "preferably," "more preferably," "particularly," "more particularly," "specifically," "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments, without any restrictions regarding the scope of the invention and without any restriction regarding the possibility of combining the features introduced in such way with other optional or non-optional features of the invention.

In a first aspect of this disclosure, a functional medical package is described. The functional medical package comprises at least one disposable package; at least one sterile container removably received inside the disposable package; and at least one subsystem configured for being at least partially inserted into a host, the subsystem being received in the sterile container. The sterile container comprises at least one insertion exit opening for the subsystem. The insertion exit opening is closed by a liner sealing the insertion exit opening. Further, the liner sealing is attached to the disposable package, such that the liner sealing is automatically peeled off when the sterile container is removed from the disposable package.

As used herein, the term "functional medical package" generally refers to an assembly of components configured for use in an arbitrary medical application. Specifically, the functional medical package may comprise at least one packaging component fully or partially enclosing or encasing at least one further component, wherein the at least one further component, as an example, may be a component which requires protection, such as mechanical protection and/or protection against moisture and/or microbial contaminations. As an example, the at least one packaging component, as will be outlined in further detail below, may comprise at least one sterile container, and the at least one further component may comprise at least one subsystem for being at least partially inserted into a host. As outlined above, the functional medical package may comprise at least one component configured for enclosing and/or protecting a content of the component for distribution, storage, safe and/or use, also referred to as a packaging component. Further, the medical package may comprise further components, such as the above-mentioned at least one subsystem. Exemplarily, the further components may be configured for conducting an arbitrary medical analysis and/or an arbitrary medical procedure.

The term "functional" may generally refer a property of an arbitrary element of having one or more functions for one or more application purposes. Thus, the medical package may exemplarily be configured for enclosing and/or protecting the content of the medical package and may additionally comprise components for conducting the medical analysis.

The term "host" generally refers to an arbitrary human being or an animal to which the functional medical package may be applied. This may be independent from the fact that the human being or animal, respectively, may be in a healthy condition or may suffer from one or more diseases. As an example, the host may be a human being or an animal suffering from diabetes. However, alternatively or additionally, this disclosure may be applied to other types of host. The host may also be referred to as patient or user.

The term "package," also referred to as a "packaging component," may generally refer to an arbitrary element or combination of elements configured for fully or partially enclosing or encasing at least one further component, such as for providing mechanical protection and/or protection against environmental influences such as moisture and/or microbial contaminations. The package may generally be or may comprise at least one arbitrary packaging component or element configured for enclosing and/or protecting a content of the element for distribution, storage, safe and/or use as described above. The term "disposable" generally refers to the property of a component or an element to be disposed of after use. Thus, the disposable element or component may be designed to be irreversibly altered or even destroyed during use, such as by mechanical deformation or by irreversible separation of components of the disposable element. Thus, the disposable package may be configured to be disposed of after use. Thus, this component may be made of at least one rigid material configured for protecting the content from mechanical stress and/or may be made of at least one tight material configured for protecting the content from moisture. The one or more materials may specially be low priced and/or easily recyclable. Still, other embodiments are feasible.

The disposable package may comprise at least one disposable package housing providing at least one interior volume and at least one disposable package opening configured such that the content of the disposable package may easily be removable. The term "housing," as used herein, generally refers to an element or component having at least one interior space and at least one wall of fully or partially surrounding the at least one interior space and providing protection to the interior space, such as one or more of a mechanical protection or a protection against environmental influences such as one or more of moisture, oxygen or microbial contaminations. The housing may generally be adapted to fully or partially surround and/or receive one or more elements in order to provide one or more of a mechanical protection, a mechanical stability, an environmental protection against moisture and/or ambient atmosphere, a shielding against electromagnetic influences or the like. The housing may also provide a basis for attachment and/or holding one or more further components or elements. Consequently, the term "disposable package housing," as used herein, refers to a housing of the disposable package.

The opening of the disposable package may have an arbitrary shape. Thus, as an example, the opening may have a round shape, a circular shape, a rectangular shape, a square shape, an oval shape or a polygonal shape. However, the size of the opening may be configured such that the sterile container may easily be removable from the disposable package through the opening. The opening may optionally but not necessarily be sealed by at least one sealing element, particularly by at least one foil or liner. As an example, the disposable package may fully or partially be embodied as a blister pack.

The terms "sealing element" and/or "sealing" as further used herein may generally refer to an arbitrary element which is configured to fully or partially concealed at least one opening and/or to fully or partially surround one or more objects to be sealed off from environmental influences such as moisture. Specifically, the sealing element or the sealing may be configured to surround the at least one element to be sealed off from the environmental influences in at least two dimensions.

The terms "liner" and/or "liner sealing" may generally refer to an arbitrary lid or lidding sealing element. Thus, the liner and/or the liner sealing may comprise at least one planar or sheet-like element which may especially extend in two dimensions. Exemplarily, the liner and/or the liner sealing may be or may comprise at least one metal and/or plastic foil. The liner and/or the liner sealing may have at least one upper surface and at least one lower surface. One or both of these surfaces may comprise at least one adhesive material.

The term "sterile" may generally refer to a property of an arbitrary object of being at least to a large extent free from all forms of life and/or other biological agents such as prions, viruses, fungi, bacteria or spore forms. Thus, the sterile object may be treated by at least one sterilization process that one or more of reduces, eliminates or deactivates the forms of life and/or of the other biological agents. The sterilization process may comprise one or more of the following techniques: heating, chemical treatment, irradiation, high pressure, and/or filtration. However, other techniques are feasible. The sterilization process may be conducted within a specified region or area of the object such as a surface of the object.

The term "container" may generally relate to an arbitrary element creating a partially or fully enclosed space that may be usable to contain, store and/or to transport objects or materials. The enclosed space may also be referred to as interior space. Thus, the container may particularly be made of a durable and/or of an at least partly rigid material such as thermoformed plastic. However, other embodiments are feasible.

Specifically, the sterile container may comprise at least one sterile container housing. Specifically, the sterile container may comprise at least one sterile container receptacle for receiving and/or holding the subsystem. Thus, the subsystem may be shaped complementary to the sterile container receptacle. Therefore, the subsystem and the sterile container may be configured to establish a form-fit connection. The term "being received" may generally refer to a condition of an object of being located or inserted fully or at least partially into a receptacle or into an opening of another element. Thus, a part of the object may be located outside of the other element. The insertion may specifically be a reversible insertion. The subsystem may be movably received in the sterile container. Thus, after insertion the object may be removable from the other element without further ado. While being received, a rigid connection between the object and the other element may be formed such that a movement of the object and the other element may at least partially be reduced in at least one direction. Specifically, the rigid connection may be established by a form-fit connection. Exemplarily, the sterile container may comprise at least one sterile container receptacle and the disposable package may comprise at least one guiding element formed as a contour.

As further used herein, the term "system" may generally refer to a group of at least two elements which may interact in order to fulfill at least one common function. The at least two elements may be handled independently or may be coupled, connectable or integratable in order to form a common component. The term "system" may also be referred to as kit or assembly. Thus, the term "subsystem" as further used herein may generally refer to a part of the system.

The subsystem may be selected from the group consisting of: an analyte sensor for detecting at least one analyte in a body tissue, specifically an electrochemical analyte sensor; a medication device for providing at least one medication to the host, specifically a cannula and more specifically a cannula for an insulin pump.

The term "analyte sensor" may generally refer to an arbitrary element which is adapted to determine at least one property of the analyte. Exemplarily, the analyte sensor may be adapted to determine a concentration of the analyte. Thus, the sensor element may particularly comprise at least one sensor material such as an electrochemical sensor material, wherein the electrochemical sensor material is adapted to perform at least one electrically detectable detection reaction in the presence of the analyte, such as an electrically detectable redox reaction.

As used herein, an "electrochemical sensor" generally is a sensor which is configured to conduct an electrochemical measurement in order to detect the at least one analyte contained in the body tissue. The term "electrochemical measurement" refers to a detection of an electrochemically detectable property of the analyte, such as an electrochemical detection reaction. Thus, for example, the electrochemical detection reaction may be detected by comparing one or more electrode potentials. The electrochemical sensor specifically may be adapted to and/or may be usable to generate at least one electrical sensor signal which directly or indirectly indicates a presence and/or an extent of the electrochemical detection reaction, such as at least one current and/or at least one voltage. For this purpose, the electrochemical sensor may provide two or more electrodes. Still, other embodiments are feasible.

As further used herein, the term "analyte" may refer to an arbitrary element, component or compound which may be present in the body fluid and the presence and/or the concentration of which may be of interest for a user, a patient or medical staff such as a medical doctor. Particularly, the analyte may be or may comprise an arbitrary chemical substance or chemical compound which may take part in the metabolism of the user or the patient, such as at least one metabolite. As an example, the at least one analyte may be selected from the group consisting of: glucose, cholesterol, triglycerides, lactate. Additionally or alternatively, however, other types of analytes are feasible.

The term "body tissue" may generally refer to an arbitrary part and/or component of a cellular organization level intermediate between cells and a complete organ of the user or the patient. Thus, the tissue may be an ensemble of similar cells from a same origin carrying out a specific function. As an example for body tissue, interstitial tissue may be named. Typically, body fluid may be present within the body tissue. Thus, as an example, the body fluid may be selected from the group consisting of blood and interstitial fluid. However, additionally or alternatively, one or more other types of body fluids may be used, such as saliva, tear fluid, urine or other body fluids.

The "medication device," as described above, may be configured for providing at least one medication to the host. Therefore, the medication device specifically may comprise at least one element configured for penetrating the skin or tissue of the host such as a cannula and/or a needle, specifically an insertion needle. Further, the medication device may comprise at least one further element configured to be placed within the tissue of the host. Exemplarily, the further element may be or may comprise at least one fluidic medium such as a medicine or may be or may comprise at least one analyte sensor such as the electrochemical sensor as described above.

The term "cannula" may generally refer to an arbitrary element which may be insertable into the body tissue of the host, particularly in order to deliver or to remove body fluid or to transfer an arbitrary element. Therefore, the cannula may specifically be a hollow tube or hollow needle. The cannula, e.g., may comprise at least one cross-section selected from the group consisting of: round, elliptical, U shaped, V shaped. Still, other embodiments are feasible. Specifically, the cannula may be a slotted cannula. The cannula may be configured to be inserted vertically or at an angle of 90° to 30° to the body tissue of the user.

Specifically, in case the medication device comprises the cannula for the insulin pump, the cannula may be configured to be inserted vertically to the body tissue of the user. On the contrary, in case the cannula comprises the analyte sensor, the cannula may be configured to be inserted at an angle of approximately 45°. Other angles, however, are feasible.

Specifically, the medication device may comprise the cannula and an insertion needle which is removably receivable in the cannula. Exemplarily, the functional medical package may comprise two of the subsystems. One of the two subsystems may be or may comprise the analyte sensor and the other one of the two subsystems may be or may comprise the medication device having the cannula and the insertion needle.

Specifically, the sterile container may comprise at least one sterile container guiding element for guiding the subsystem during insertion into a tissue of the host. The term "guiding element" as further used herein may refer to a component or part of an object which is configured to interact with a counterpart guiding element in order to form a connection. Thus, the guiding element and the counterpart guiding element may be complementary elements configured for forming the connection. Exemplarily, the guiding element may comprise one or more guide rails and the counterpart guiding element may have complementary shaped receptacles. However, other embodiments are feasible. Specifically, the sterile container guiding element may be formed as guide rails facing an interior space of the sterile container and the subsystem may comprise complementary receptacles.

As described above, the sterile container comprises the at least one insertion exit opening for the subsystem. Specifically, the sterile container housing may comprise the insertion exit opening. As further used herein, the term "insertion exit opening" may generally refer to an arbitrary opening as described above. The insertion exit opening may be configured to receive the subsystem at least partially, specifically at least to a large extent.

The sterile container may further comprise at least one drive opening for enabling an actuator of an inserter to enter the sterile container and to engage with the subsystem for insertion into the host. Specifically, the drive opening may be shaped as an elongate slit having a lower end being located near the supporting surface of the sterile container housing and an upper end opposing the lower end.

As further used herein, the term "actuator" may refer to an arbitrary element which is configured to move or control an arbitrary mechanism or a system. The actuator may be operated by a source of energy, typically electric current or mechanical pressure and may convert energy into motion. The actuator may be selected from the group consisting of:

a mechanical actuator, an electromagnetic actuator, a pneumatic actuator, a hydraulic actuator. However, other kinds of actuators may be applied.

As further used herein, the term "inserter" generally refers to an arbitrary element which is configured to insert an arbitrary medical component such as the analyte sensor or the fluidic medium into the tissue of the host. Therefore, the inserter may be configured to receive the subsystem and to transfer the subsystem to the tissue of the host. For this purpose, the inserter may comprise the actuator. Thus, the inserter may be configured for fulfilling multiple functions, e.g., in addition to the transfer of the subsystem to the tissue of the host, the function of fully or partially inserting the subsystem into the tissue of the host.

The inserter may comprise at least one drive arm. As further used herein, the term "drive arm" may refer to an arbitrary element configured for supporting a movement of another object in at least one direction. Specifically, the drive arm may apply a force to the other object in the at least one direction. The drive arm, as an example, may be or may comprise a lever arm. The drive arm may be applied to exert a large force over a small distance at one end by exerting only a small force over a greater distance at the other. Therefore, the drive arm may also be referred to as "lever."

The drive arm may be configured to be inserted into the sterile container, specifically via the drive opening of the sterile container. Thus, the drive arm may have a narrow and/or an elongate shape. The drive arm may take at least two different positions. In an initial position, the drive arm may touch the upper end of the drive opening. Therefore, the initial position may also be referred to as upper position. Further, the drive arm may take a final positon wherein the drive arm may touch the lower end of the drive opening. Within this position, components of the subsystem such as the cannula as described above may be at least partially inserted into the tissue of the host. Thus, the final position may also be referred to as lower position. Specifically for this purpose, the drive arm may have at least one supporting surface configured for attaching to the components of the subsystem. The force as described above may be exerted on the components via the supporting surface of the drive arm.

The terms "upper position," "initial position," "lower position" and "final position" may be considered as description without specifying an order and without excluding a possibility that the inserter may be movable to several kinds of upper, lower, initial and final positions. As an example, however, the inserter may be moveable from precisely one upper position or initial position into precisely one lower position or final position and vice versa, thereby performing a digital movement from a first state to a second state or vice versa.

The drive opening may be sealed by at least one drive sealing element or seal, specifically a liner. The drive sealing element may be or may comprise at least one foil. A rim of the drive sealing element may comprise an arbitrary attachment component located on at least one plane surface of the drive sealing element. Specifically, the attachment component may encircle the drive sealing element continuously in order to enable a tight sealing of an arbitrary opening. Therefore, the drive opening may comprise at least one sealing surface around the drive opening configured for attachment of the drive sealing element. Particularly, the drive sealing element may be configured to be penetrable by the actuator. The drive sealing element may be configured to be cut open, particularly by the drive arm of the inserter, whereas the liner sealing is automatically peeled off. Thus, the liner sealing is configured for being peeled off, whereas the drive sealing element may be configured for being peeled off, too, and/or for being cut open, such as by a drive arm of the inserter and/or by another cutting mechanism, such as an optional cutting mechanism comprised by the medical device.

As described above, the insertion exit opening is closed by the liner sealing. Further, the liner sealing is attached to the disposable package such that the liner sealing is automatically peeled off when the sterile container is removed from the disposable package. As further used herein, the term "automatically peeled off" may refer to a procedure wherein an arbitrary sealing element is removed from an attachment surface without taking measures and/or in conjunction with other measures the main purpose of which is not the peeling off of the liner sealing. As an example, the sterile container may be disposed in the disposable package such that the sterile container may be removed from the disposable package in a removal direction. As an example, the disposable package made comprise at least one guiding element such as at least one guiding rail which guides the sterile container during removal from the disposable package. The liner sealing may, on a first side, be attached to the insertion exit opening such that insertion exit opening is closed by the liner sealing and, on a second side, be attached to the disposable package. In between, the liner sealing may, as an example, be folded, such as by having an S-shape and/or by having a U-shape. When the sterile container is removed from the disposable package, such as guided by the at least one optional guiding element, the liner sealing may be held by the disposable package and, thus, the liner sealing may be peeled off from the insertion exit opening due to the force required for removing the sterile container from the disposable package.

The upper surface of the liner sealing may be non-adhesive and the lower surface may comprise the adhesive material. Thereby, the linear sealing may be positioned on the disposable package in a two layer manner. One part of the lower surface of the liner sealing may be attached to a surface of the disposable package and another part of the lower surface of the liner sealing may be attached on a surface of the sterile container, particularly of the sterile container housing whereby one part of the upper surface may face another part of the upper, non-adhesive surface. Thus, when the sterile container is removed from the disposable package in a linear direction the sterile container may detach from the liner sealing while the liner sealing may stay attached to the disposable package. The liner sealing may unfold and form a single strip.

Specifically, the drive sealing element and the liner sealing may be one single element. Alternatively, the drive sealing element and the liner sealing may be separate sealing elements.

The inserter and the sterile container may be attached to each other by at least one form-fit connection such as by a catch-mechanism. Thereby, the inserter may comprise one or more clamping elements which may be configured to engage in complementary receptacles of the sterile container.

The functional medical device may further comprise at least one body mount. The term "body mount" may generally refer to an arbitrary device which is attachable to the skin of the host. Thus, the body mount may comprise at least one attachment component which is capable of connecting the body mount to the skin, such as at least one adhesive surface and/or at least one adhesive strip or plaster. The body mount may further comprise at least one body mount opening configured as outlet for the components of the subsystem which may be inserted into the skin of the host as described above.

The sterile container may be attached to the body mount, preferably with a gap in between the sterile container and the body mount, more preferably with a gap receiving the liner sealing. The liner sealing may be at least partially located in between the sterile container and the body mount. Further, the sterile container and the body mount may be removable from the disposable package as a unit.

In a further aspect of this disclosure, a medical device for inserting at least one subsystem into a host is disclosed. As further used herein, the term "medical device" may refer to an arbitrary device configured for conducting at least one medical analysis and/or at least one medical procedure.

The medical device comprises:
  at least one functional medical package according to any one of the preceding embodiments; and
  at least one inserter configured for inserting the subsystem into the host.

The functional medical package and the inserter may be embodied as outlined above, according to one or more of the embodiments listed above or listed in further detail below. It shall be noted, however, that other embodiments are feasible.

In a further aspect of this disclosure, a method of manufacturing the functional medical package and a method for picking up a subsystem configured for being at least partially inserted into a host by an inserter according to any embodiment as described above or as will further be described below are disclosed.

The methods comprise the method steps as given in the independent claims and as listed as follows. The method steps may be performed in the given order. However, other orders of the method steps are feasible. Further, one or more of the method steps may be performed in parallel and/or in a timely overlapping fashion. Further, one or more of the method steps may be performed repeatedly. Further, additional method steps may be present which are not listed.

The method of manufacturing the functional medical package comprises:
  providing the disposable package;
  providing the sterile container with the subsystem received therein, with the liner sealing closing the insertion exit opening;
  removably receiving the sterile container inside the disposable package; and
  attaching the liner sealing to the disposable package.

The functional medical package may be embodied as outlined above, according to one or more of the embodiments listed above or listed in further detail below. It shall be noted, however, that other embodiments are feasible.

Specifically, the functional medical package may comprise the body mount as described above and while removably receiving the sterile container inside the disposable package the sterile container may be attached to the body mount, preferably by at least one form-fit connection.

The method may further comprise at least one sterilization step for sterilizing the sterile container with the subsystem received therein. Specifically, the sterilization step may be performed before removably receiving the sterile container inside the disposable package.

The sterilization step may comprise at least one step of radiation sterilization. Thereby, the subsystem received in the sterile container may be sterilized by radiation, preferably by radiation selected from the group consisting of electron beam radiation, x-rays and gamma rays.

The method for picking up a subsystem configured for being at least partially inserted into a host by an inserter comprises:
  I. providing at least one functional medical package according to any one of the preceding embodiments referring to a functional medical package;
  II. connecting at least one inserter to the functional medical package, wherein the inserter engages with the sterile container of the functional medical package;
  III. removing the inserter from the disposable package of the functional medical package, wherein the sterile container remains engaged with the inserter and wherein the liner sealing is peeled off from the insertion exit opening of the sterile container during removing the inserter from the disposable package.

During step II., the inserter and the sterile container may be attached to each other by at least one form-fit connection, preferably by a catch mechanism. Therefore, the sterile container may comprise further sterile container receptacles configured to be engaged by clamping elements of the inserter as described above.

The proposed functional medical package, the medical device for inserting at least one subsystem into a host, the method of manufacturing the functional medical package the method for picking up a subsystem configured provide many advantages over known devices and methods.

Usually, in medical devices, specifically in assemblies such as assemblies with electrochemical sensors, the subsystem, specifically the sensor, generally needs to be sterilized by electron beam sterilization, whereas other components like electronic components and/or adherent components are generally sterilized via gas sterilization. Hence, parts of the medical device generally need to be handled and sterilized separately. In the state of the art it is known to package the subsystem, specifically the sensor, assembled inside the inserter for sterilization, to use a sterile capsule for the subsystem, specifically the sensor, with septum in combination with a piercing mechanism or to use separate packages that the user or the patient may assemble.

In order to reduce the electron beam sterilization to the subsystem, specifically to the sensor only, the sterile container may only house the subsystem, specifically the sensor. This generally allows to simplify handling in production and to reduce costs for sterilization. To further simplify handling, the sterile container may be incorporated into the disposable package such that the liner sealing of the sterile container on the insertion exit opening is automatically peeled off on removing the disposable package.

The sterile container with the liner sealing may particularly be useful in combination with the functional medical package for disposables of a multi disposable inserter. Furthermore, the functional disposable package does not need to maintain sterile conditions. In principle, a sealing element closing the functional medical package such as a foil may be disregarded, which may further simplify handling.

The functional medical package, specifically the disposable package, may have a minimal necessary construction volume for components of the functional medical package which need to be sterilized. Consequently, the sterilization process may specifically be low-priced. Specifically, subcutaneous glucose sensor elements or systems, specifically configured for conducting continuous glucose measurements, as well as cannulas for an insulin pump. Openings of the functional medical package, specifically of the sterile container, may be sealed in a sterile manner via the sealing elements such as the liner sealing and may be opened during usage. This may be conducted by peeling the liner sealing off or by breaking through the liner sealing.

The functional medical package may be easily transportable and may be handled under normal installation conditions during manufacturing the functional medical package. Cleanroom conditions may not be necessary. In order to reduce a number of handling steps for the user or the patient, the liner sealing may be peeled off while the sterile container is removed form the disposable package. Therefore, one end of the liner sealing may exemplarily be fixed on one surface of the disposable package which may lead to a peeling off the liner sealing during removing the sterile container from the disposable package. The user or the patient does not need to conduct a further handling step.

The sterile container may be sealed via the liner sealing and the drive opening sealing. Specifically, the drive opening sealing may be slit by the inserter the liner sealing may be removed. This step may be conducted automatically during removing of the sterile container from the disposable package. Therefore, the liner sealing may be attached to the disposable package as a loop and may be attached at one end of the disposable package.

The disposable package does not necessarily need to be designed in a gastight manner. Therefore, an opening within the disposable package may be realizable. The sterile container may be removed from the disposable package via the inserter and the liner sealing may be peeled off automatically. Therefore, there may be a minimal distance between the body mount and a bottom side of the sterile container. Exemplarily, this distance may be realized via retaining pins. The retaining pins may be located on side walls of the sterile container. The drive opening may be slit during inserting of the inserter within the disposable package.

Summarizing the findings of this disclosure, the following embodiments are preferred:

Embodiment 1

A functional medical package, comprising
a) at least one disposable package;
b) at least one sterile container removably received inside the disposable package; and
c) at least one subsystem configured for being at least partially inserted into a host, the subsystem being received in the sterile container;
  wherein the sterile container comprises at least one insertion exit opening for the subsystem,
  wherein the insertion exit opening is closed by a liner sealing on the insertion exit opening,
  wherein the liner sealing is attached to the disposable package, such that the liner sealing is automatically peeled off when the sterile container is removed from the disposable package.

Embodiment 2

The functional medical package according to the preceding embodiment, wherein the subsystem is selected from the group consisting of: an analyte sensor for detecting at least one analyte in a body tissue, specifically an electrochemical analyte sensor; a medication device for providing at least one medication to the host, specifically a cannula and more specifically a cannula for an insulin pump.

Embodiment 3

The functional medical package according to the preceding embodiment, wherein the medication device comprises the cannula and an insertion needle which is removably receivable in the cannula.

Embodiment 4

The functional medical package according to any one of the preceding embodiments, wherein the sterile container comprises at least one sterile container housing having the insertion exit opening, and wherein the sterile container further comprises at least one drive opening for enabling an actuator of an inserter to enter the sterile container and to engage with the subsystem for insertion into the host.

Embodiment 5

The functional medical package according to the preceding embodiment, wherein the drive opening is sealed by at least one drive sealing element, specifically a liner, preferably a drive sealing element which may be penetrated by the actuator.

Embodiment 6

The functional medical package according to the preceding embodiment, wherein the drive sealing element and the liner sealing are one single element.

Embodiment 7

The functional medical package according to any one of the two preceding embodiments, wherein the drive sealing element and the liner sealing are separate sealing elements.

Embodiment 8

The functional medical package according to any one of the three preceding embodiments, wherein the drive sealing element is configured to be cut open, particularly by at least one drive arm of the inserter and/or by a cutting mechanism of the inserter.

Embodiment 9

The functional medical package according to any one of the preceding embodiments, wherein the disposable package comprises a disposable package opening through which the sterile container is removable from the disposable package.

Embodiment 10

The functional medical package according to the preceding embodiment, wherein the opening is sealed by at least one sealing element, preferably by at least one liner.

Embodiment 11

The functional medical package according to any one of the preceding embodiments, further comprising at least one body mount configured for attachment to a skin of the host.

Embodiment 12

The functional medical package according to the preceding embodiment, wherein the sterile container is attached to the body mount, preferably with a gap in between the sterile container and the body mount, more preferably with a gap receiving the liner sealing.

Embodiment 13

The functional medical package according to the preceding embodiment, wherein the sterile container is attached to the body mount via a form-fit connection.

Embodiment 14

The functional medical package according to any one of three the preceding embodiments, wherein the sterile container and the body mount are removable from the disposable package as a unit.

Embodiment 15

The functional medical package according to any one of the three preceding embodiments, wherein the liner sealing is at least partially located in between the sterile container and the body mount.

Embodiment 16

The functional medical package according to any one of the preceding embodiments, wherein the subsystem is movably received in the sterile container.

Embodiment 17

The functional medical package according to the preceding embodiment, wherein the sterile container comprises at least one guiding element for guiding the subsystem during insertion into a tissue of the host.

Embodiment 18

A medical device for inserting at least one subsystem into a host, the medical device comprising:
  at least one functional medical package according to any one of the preceding claims; and
  at least one inserter configured for inserting the subsystem into the host.

Embodiment 19

A method of manufacturing the functional medical package according to any one of the preceding embodiments referring to a functional medical package, the method comprising:
  providing the disposable package;
  providing the sterile container with the subsystem received therein, with the liner sealing closing the insertion exit opening;
  removably receiving the sterile container inside the disposable package; and
  attaching the liner sealing to the disposable package.

Embodiment 20

The method according to the preceding embodiment, wherein the method further comprises at least one sterilization step for sterilizing the sterile container with the subsystem received therein.

Embodiment 21

The method according to the preceding embodiment, wherein the sterilization step is performed before removably receiving the sterile container inside the disposable package.

Embodiment 22

The method according to any one of the two preceding embodiments, wherein the sterilization step comprises at least one step of radiation sterilization, wherein the subsystem received in the sterile container is sterilized by radiation, preferably by radiation selected from the group consisting of electron beam radiation, x-rays and, and gamma rays.

Embodiment 23

The method according to any one of the three preceding embodiments, wherein at least one body mount configured for attachment to a skin of the host is provided, wherein the sterile container is attached to the body mount, preferably by at least one form-fit connection, while removably receiving the sterile container inside the disposable package.

Embodiment 24

A method for picking up a subsystem configured for being at least partially inserted into a host by an inserter, the method comprising:
  I. providing at least one functional medical package according to any one of the preceding embodiments referring to a functional medical package;
  II. connecting at least one inserter to the functional medical package, wherein the inserter engages with the sterile container of the functional medical package;
  III. removing the inserter from the disposable package of the functional medical package, wherein the sterile container remains engaged with the inserter and wherein the liner sealing is peeled off from the insertion exit opening of the sterile container during removing the inserter from the disposable package.

Embodiment 25

The method according to the preceding embodiment, wherein during step II., the inserter and the sterile container are attached to each other by at least one form-fit connection, preferably by a catch mechanism.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following description. Rather, the embodiments are chosen and described so that others skilled in the art may appreciate and understand the principles and practices of this disclosure.

FIGS. 1A to 1D show an embodiment of an exemplary disposable package 110 in different perspective views.

The disposable package 110 may be configured for enclosing and/or protecting a content of the disposable package 110 and may further be configured to be disposed after use. The disposable package 110 may have a disposable package housing 112. The disposable package housing 112 may provide at least one interior volume 114. Thus, the disposable package housing 112 may specifically be made of at least one rigid material and/or of at least one gastight material in order to protect contents of the interior volume 114 from mechanical stress and/or moisture.

Specifically, the disposable package 110 may be box-shaped. Further, the disposable package 110 may have at least one disposable package opening 116. The disposable package opening 116 may exemplarily have a rectangular shape. Specifically, the disposable package opening 116 may be configured such that a content of the disposable package 110 may easily be removable.

Figure 1:
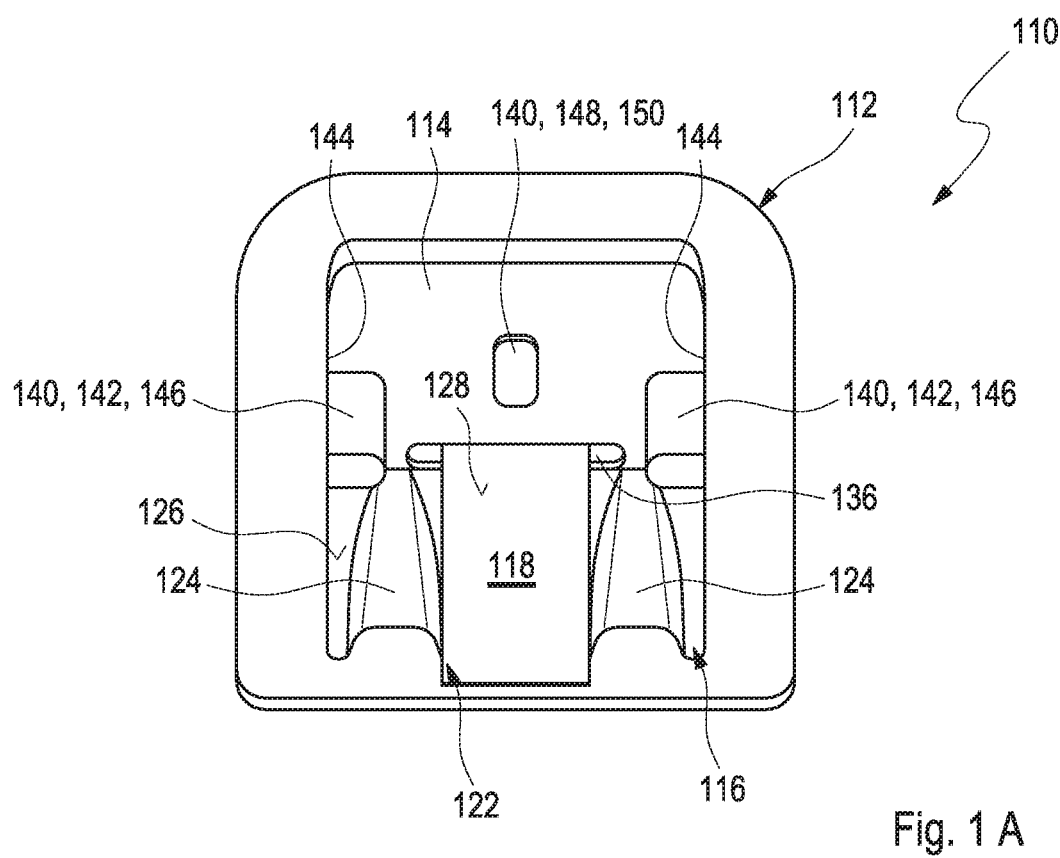
FIGS. 1A to 1D show an embodiment of an exemplary disposable package in different perspective views.
Figure 1:
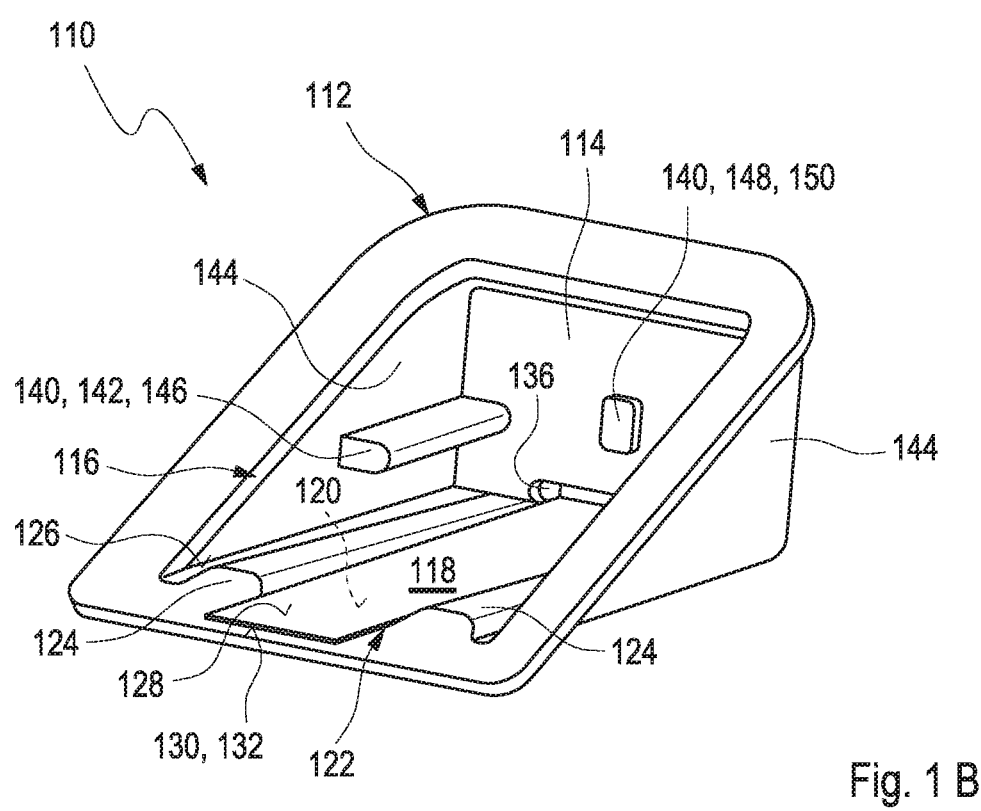
Figure 1C:
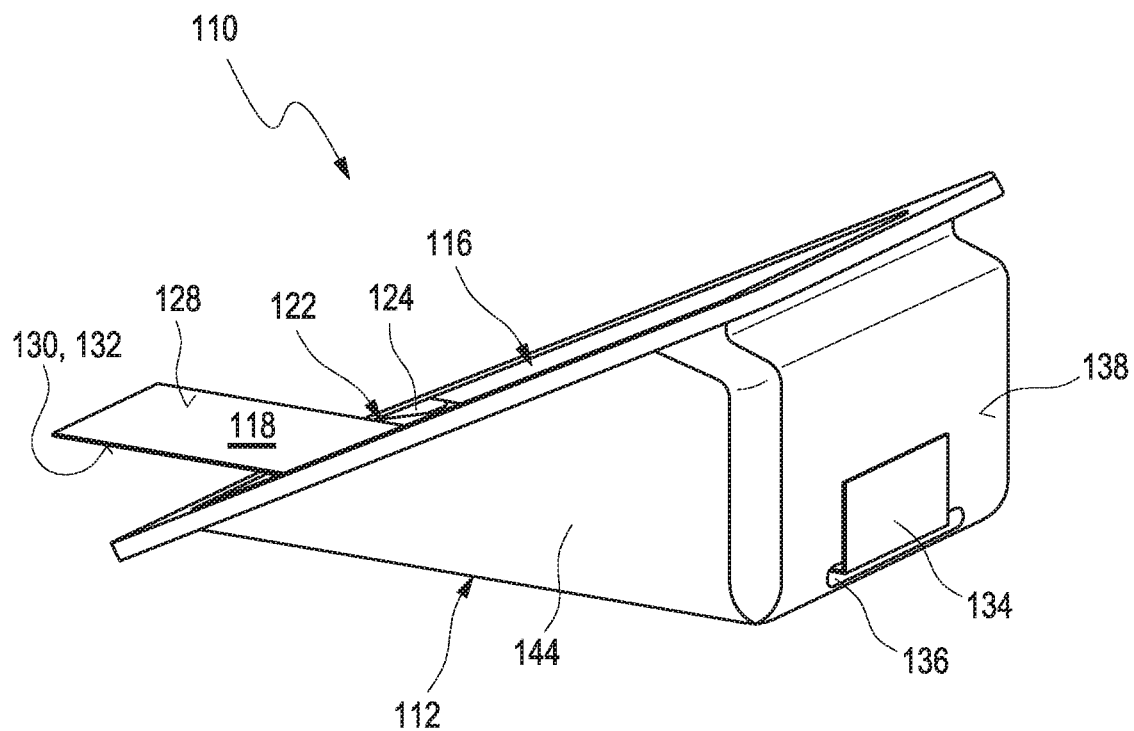
Figure 1D:
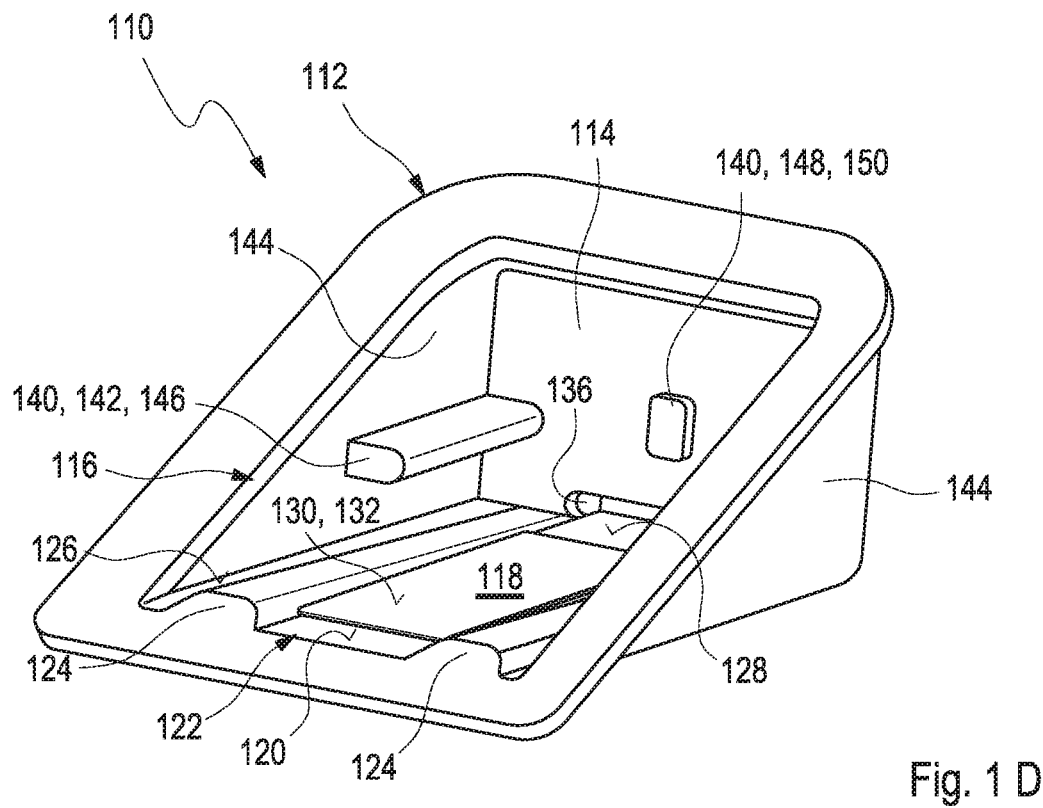

Further, a liner sealing (also referred to as a "liner") 118 is illustrated in FIGS. 1A to 1D. The liner sealing 118 may be located on a disposable package supporting surface 120. Specifically, the disposable package supporting surface 120 may be located within a receptacle 122 of the disposable package 110. The receptacle 122 may be formed by at least two racks 124 which are located parallel to each other on a surface 126 of the disposable package 110. The linear sealing 118 may be strip-shaped and may be made of a flexible foil. Further, the linear sealing 118 may have at least one upper surface 128 and at least one lower surface 130. The lower surface 130 may at least partially be an adhesive surface 132. The upper surface 128 may at least to a large extent free from adhesive materials. Exemplarily, only at one end 134 of the liner sealing 118 an adhesive material may be located at the upper surface 128. The end 134 may be lead through a passage opening 136 of the disposable package 110 and may be attached to an outer surface 138 of the disposable package 110. FIGS. 1A to 1C show the disposable package 110 in a state wherein a sterile container 152 as will further be discussed below may be removed from the disposable package 110. In a state before the sterile container 152 is removed form the disposable package 110, as depicted in FIG. 1D, the liner sealing 118 may be positioned on the disposable package 110 in a two layer manner. Parts of the upper surface 128 may face each other.

Further, the disposable package 110 may comprise several disposable package guiding elements 140. Specifically, the disposable package 110 may comprise two first disposable package guiding elements 142. The first disposable package guiding elements 142 may be located at side walls 144 of the disposable package 110 facing the interior volume 114. The first disposable package guiding elements 142 may be formed as guide-rails 146. The guide-rails 146 may be configured to guide an inserter 222 as will further be described below in more detail. Moreover, the disposable package 110 may comprise at least one second disposable package guiding element 148. The second disposable package guiding element 148 may be formed as a contour 150 which may be complementary to a receptacle. Specifically, the second disposable package guiding element 148 may be configured to establish a form-fit connection to the sterile container 152 as will further be described below in more detail.

Figure 2:
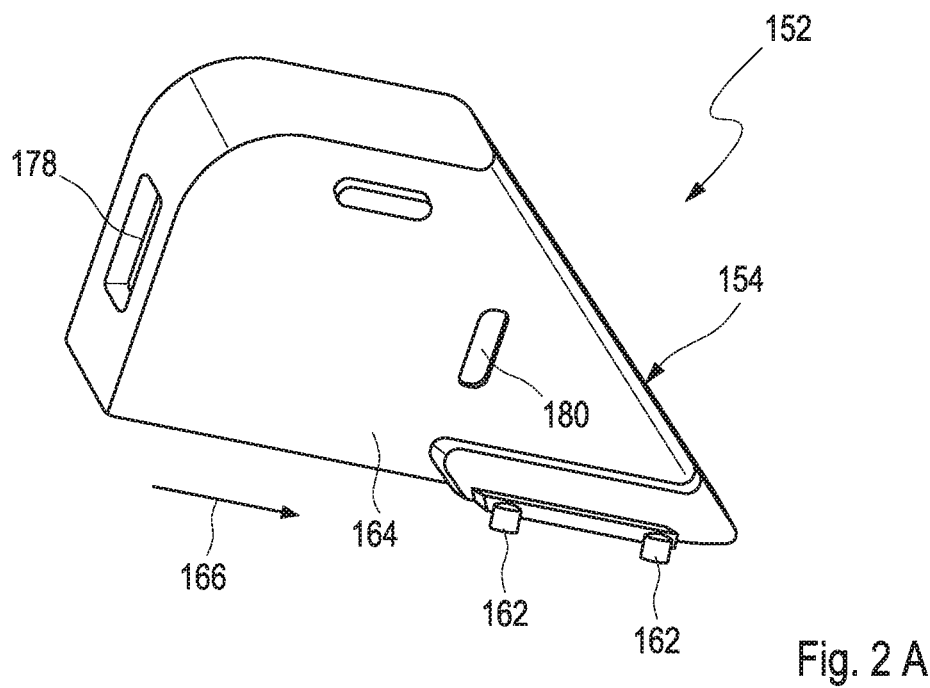
FIGS. 2A to 2C show an exemplary embodiment of a sterile container in different perspective views.
Figure 2:
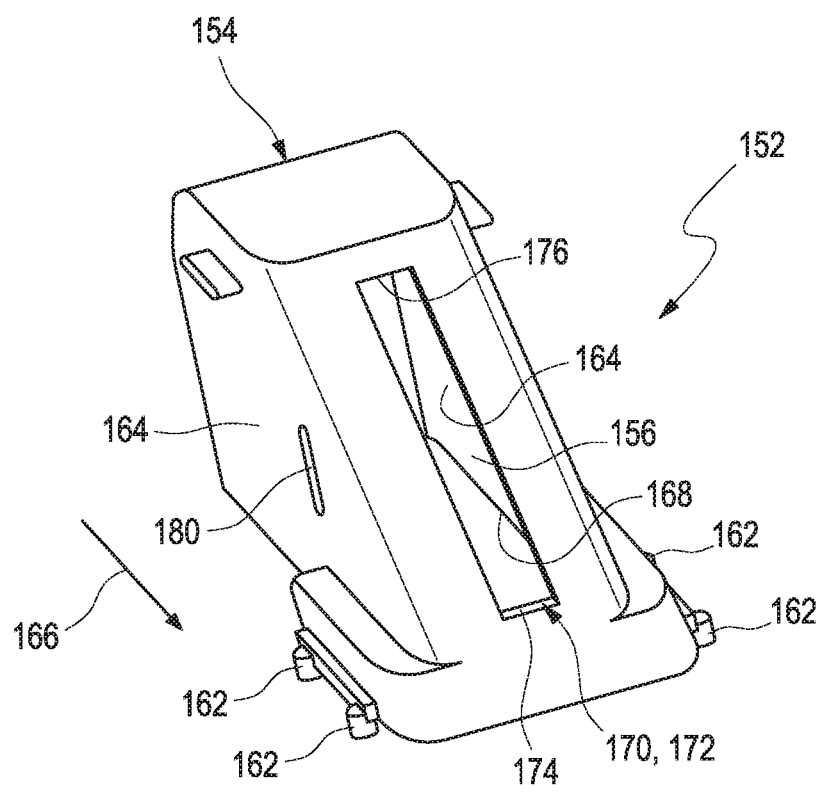
Figure 2:
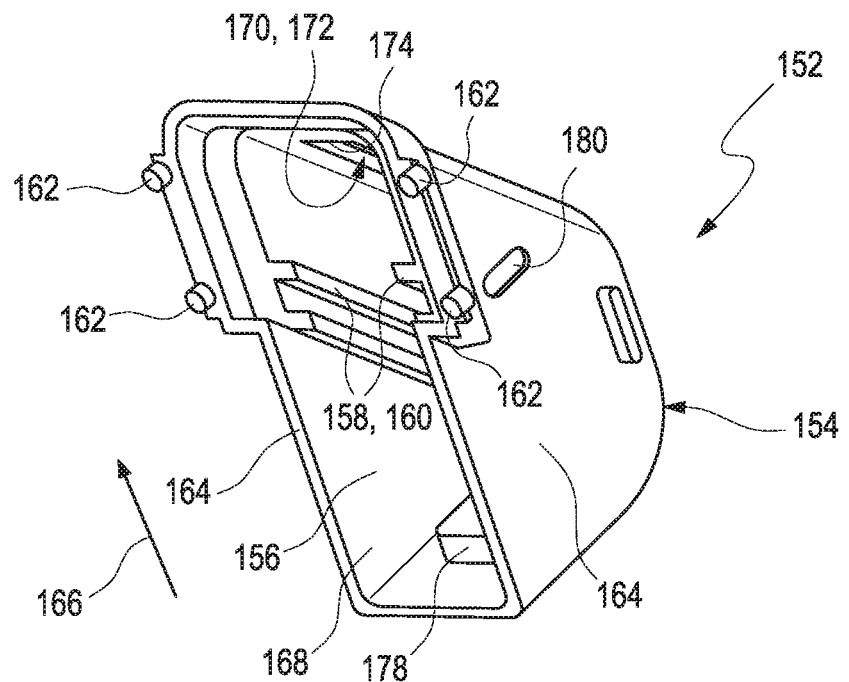

FIGS. 2A to 2C show an exemplary embodiment of a sterile container 152 in different perspective views.

The sterile container 152 may comprise at least one sterile container housing 154. The housing 154 may have one or more interior spaces 156 configured for receiving one or more further elements or components. Specifically, the sterile container 152 may comprise at least one sterile container guiding element 158 facing the interior space 156 as illustrated in FIG. 2C. The sterile container guiding elements 158 may be formed as guide rails 160 and may be configured to lead another object, specifically a subsystem 202, with complementary receptacles as will further be described below in at least one direction.

Further, the sterile container 152 may comprise at least two, specifically at least four retaining pins 162. The retaining pins 162 may be located on sterile container side walls 164 of the sterile container 152. The retaining pins 162 may be configured to attach the sterile container 152 to another element such as to a body mount 192 which will further be described below in more detail. The other element may be formed essentially planar and the sterile container guiding elements 158 may run in an angle of 30° to 90° to a direction of extension 166 to the subsystem 202.

The sterile container 152 comprises at least one insertion exit opening 168 as illustrated in FIGS. 2B and 2C. The insertion exit opening 168 may be configured to receive the subsystem 202 as will further be described below in more detail at least to a large extent. Thus, a shape of the interior space 156 of the sterile container 152 may be complementary to the subsystem 202.

Moreover, the sterile container 152 may comprise at least one drive opening 170. The drive opening 170 may be shaped as an elongate slit 172. Therefore, the drive opening 170 may have a lower end 174 and an upper end 176. The drive opening 170 may be configured for enabling an actuator of the inserter 222 to enter the sterile container 152. Further details may be given below in more detail.

The sterile container 152 may comprise a sterile container receptacle 178 configured to receive the second disposable package guiding element 142 of the disposable package 110 as described within FIGS. 1A to 1D. Further, the sterile container 152 may have further sterile container receptacles 180, specifically located on the sterile container side walls 164. The further sterile container receptacles 180 may be configured to receive one or more clamping elements 246 of the inserter 222 as will further be discussed below in more detail.

Figure 3:
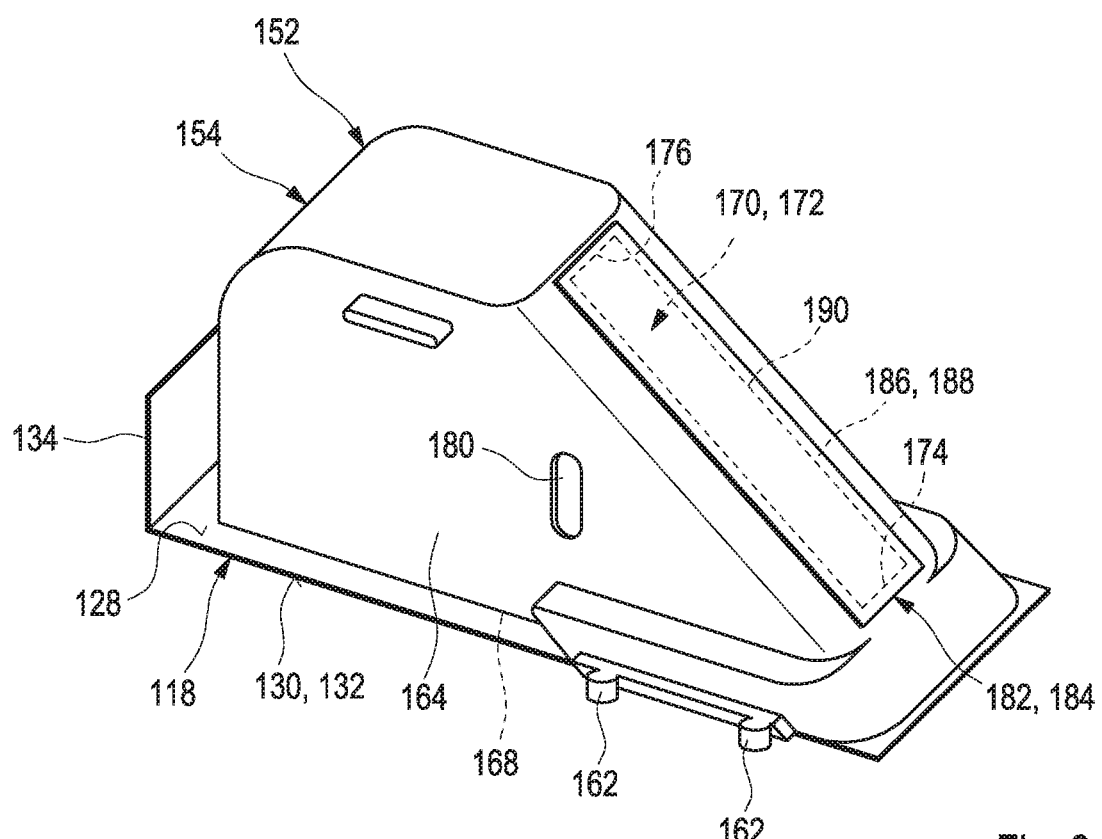
FIGS. 3A to 3C show an exemplary embodiment of a sterile container in various perspective views, wherein the sterile container in FIGS. 3B and 3C is shown with a body mount.
Figure 3:
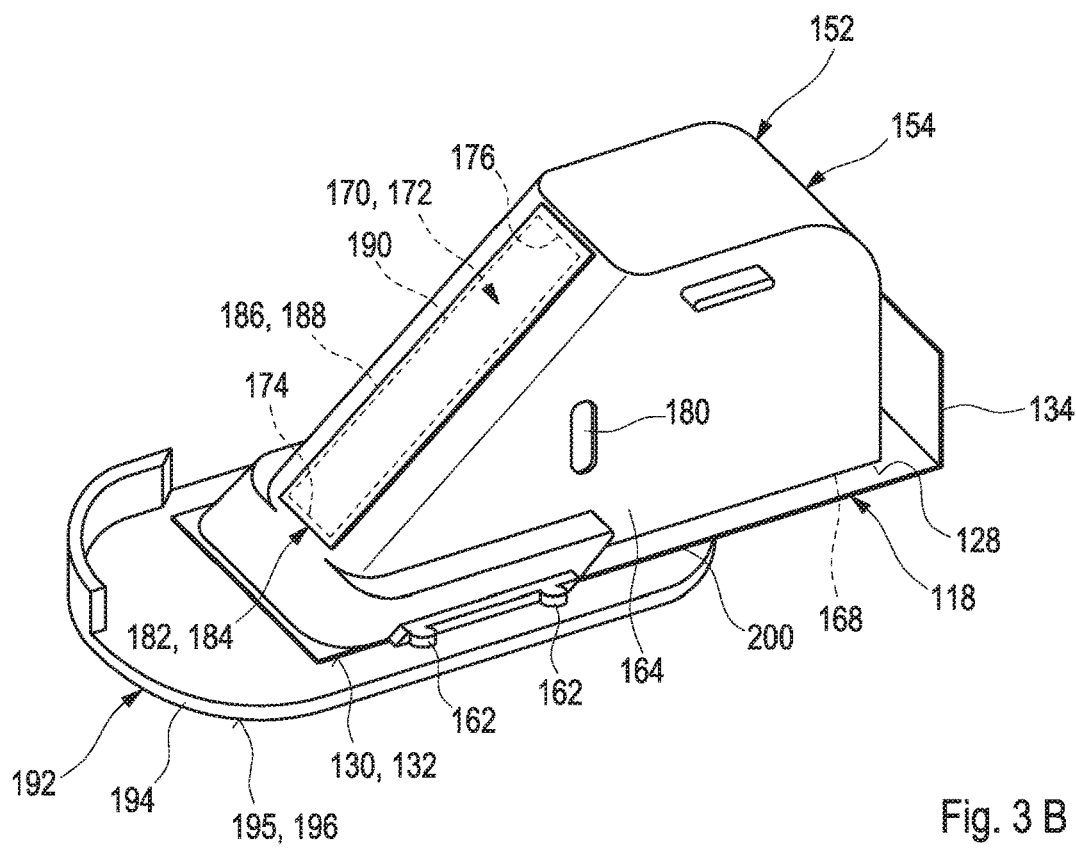
Figure 3:
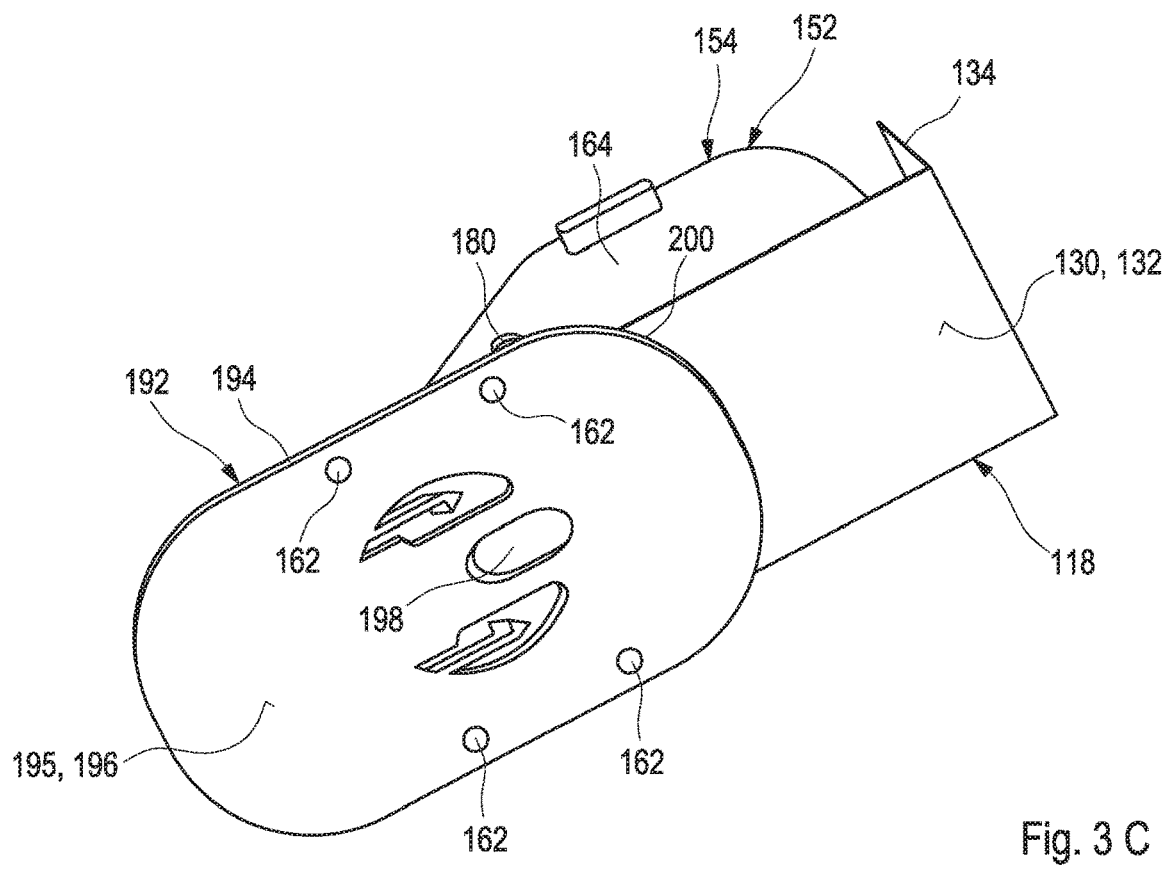

FIGS. 3A to 3C show an exemplary embodiment of a sterile container 152 in a perspective view, wherein the sterile container 152 in FIGS. 3B and 3C is shown with a body mount 192.

The sterile container 152 corresponds at least in large parts to the sterile container 152 as illustrated in FIGS. 2A to 2C. Thus, reference may be made to the description of FIGS. 2A to 2C below.

The insertion exit opening 168 may be sealed with the liner sealing 118 as described within FIGS. 1A to 1D.

The drive opening 170 may be sealed with at least one drive sealing element 182. The drive sealing element 182 may be made of a material identically to the liner sealing 118. The drive sealing element 182 may exemplarily be made of or may comprise a plastic foil 184. A rim 186 of the drive sealing element 182 may comprise at least one attachment component 188. Specifically, the attachment component 188 may encircle the drive sealing element 182 continuously. Thus, the sterile container housing 154, specifically the drive opening 170, may comprise at least one sealing surface 190 around the drive opening 170 configured for attachment of the drive sealing element 182.

The sterile container 152, specifically the sterile container housing 154, may be attached to at least one body mount 192. The body mount 192 may comprise at least one body mount base 194. Further, the body mount 192, specifically the body mount base 194, may comprise at least one adhesive surface 195, specifically a plaster 196, configured for attachment of a skin of the host. Beyond this, the body mount 192 may comprise at least one body mount opening 198 configured as outlet for components of the subsystem 202 as will further be described below.

Specifically, the body mount 194 may be attached to the sterile container 152 with a gap 200 between the body mount 194 and the sterile container 152. The gaps 200 may receive the liner sealing 118. Thus, the liner sealing 118 may at least partially be located between the sterile container 152 and the body mount base 194.

Figure 4:
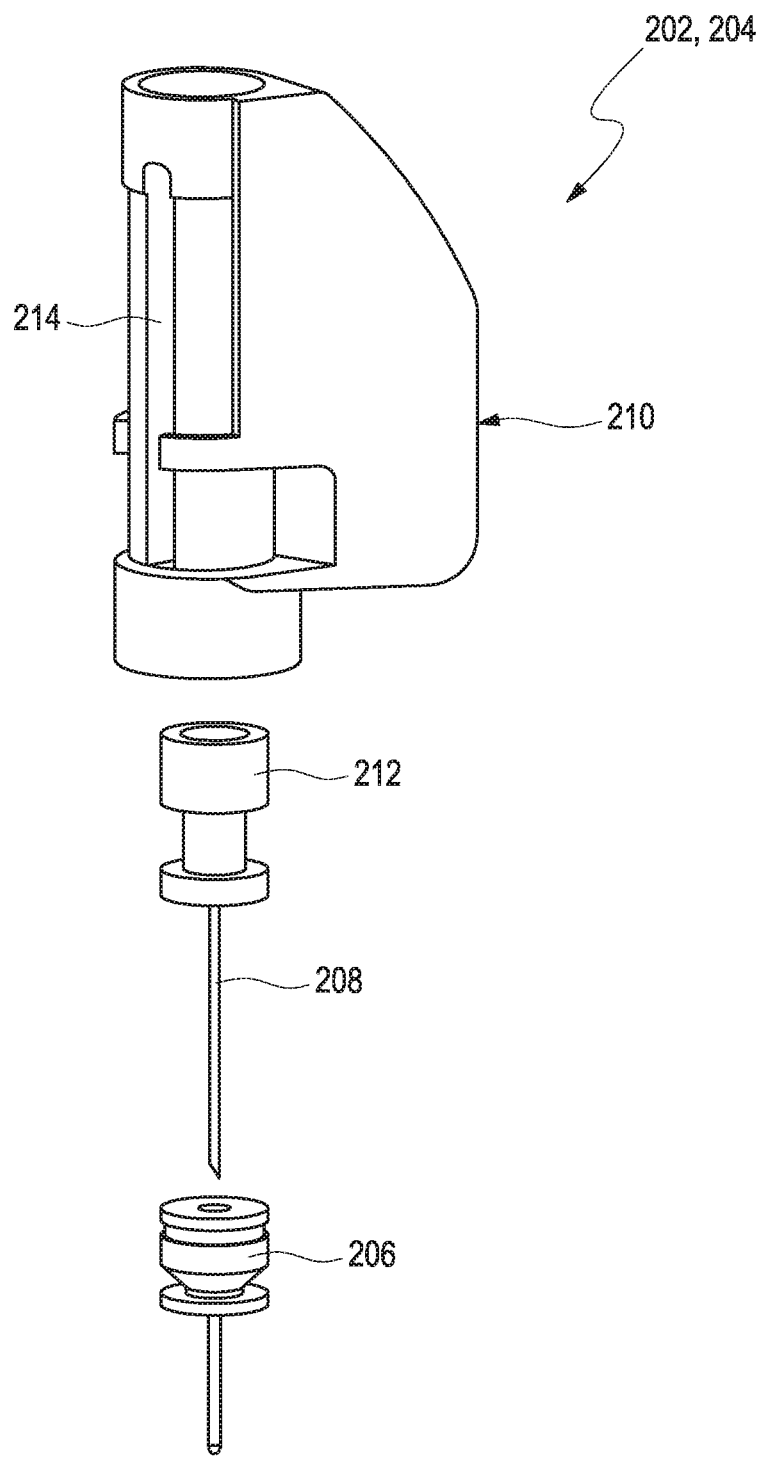
FIGS. 4A to 4C show an exemplary embodiment of a subsystem in a disassembled view (FIG. 4A) and in different cross-sectional views (FIGS. 4B and 4C)
Figure 4:
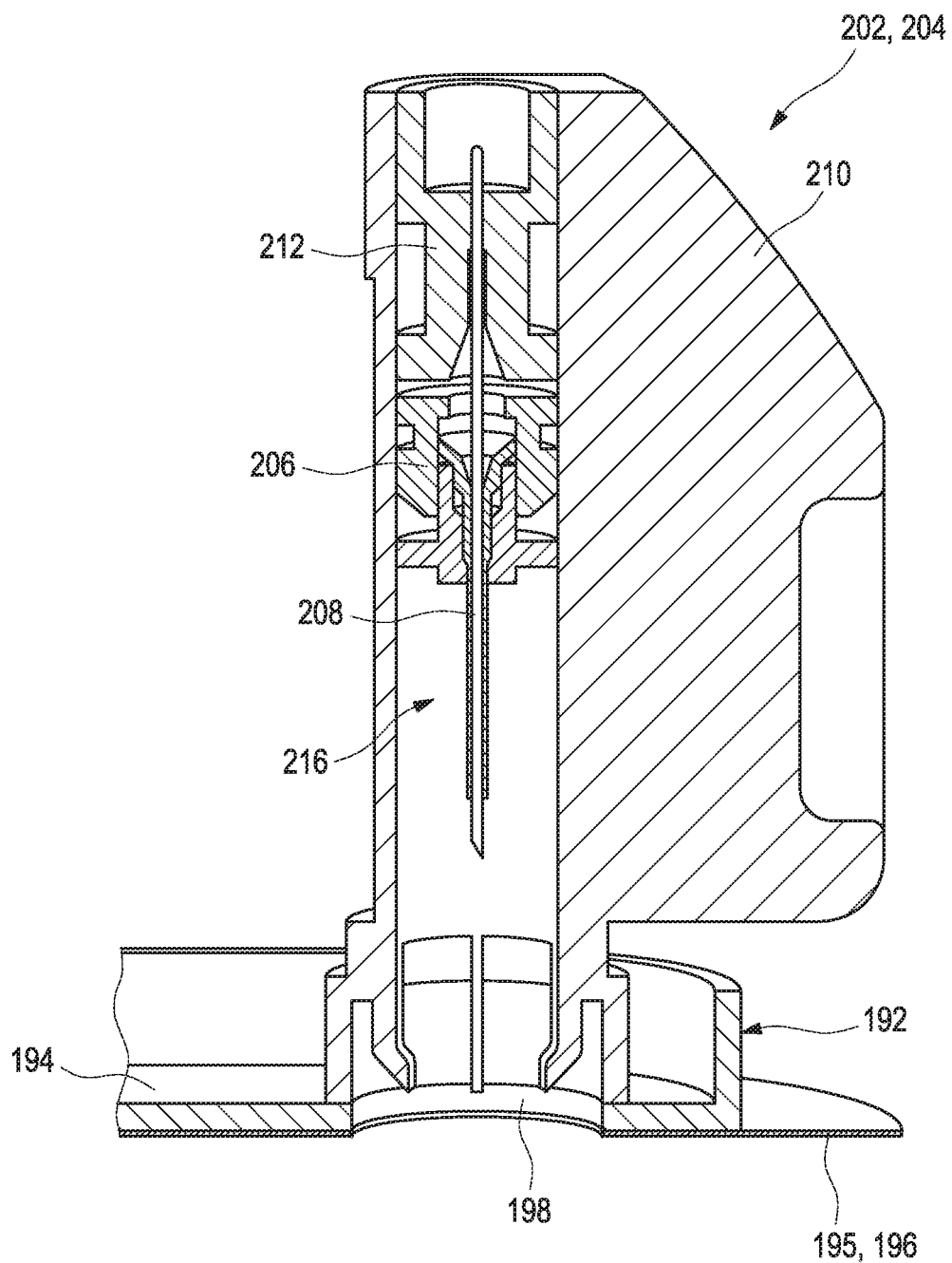
Figure 4:
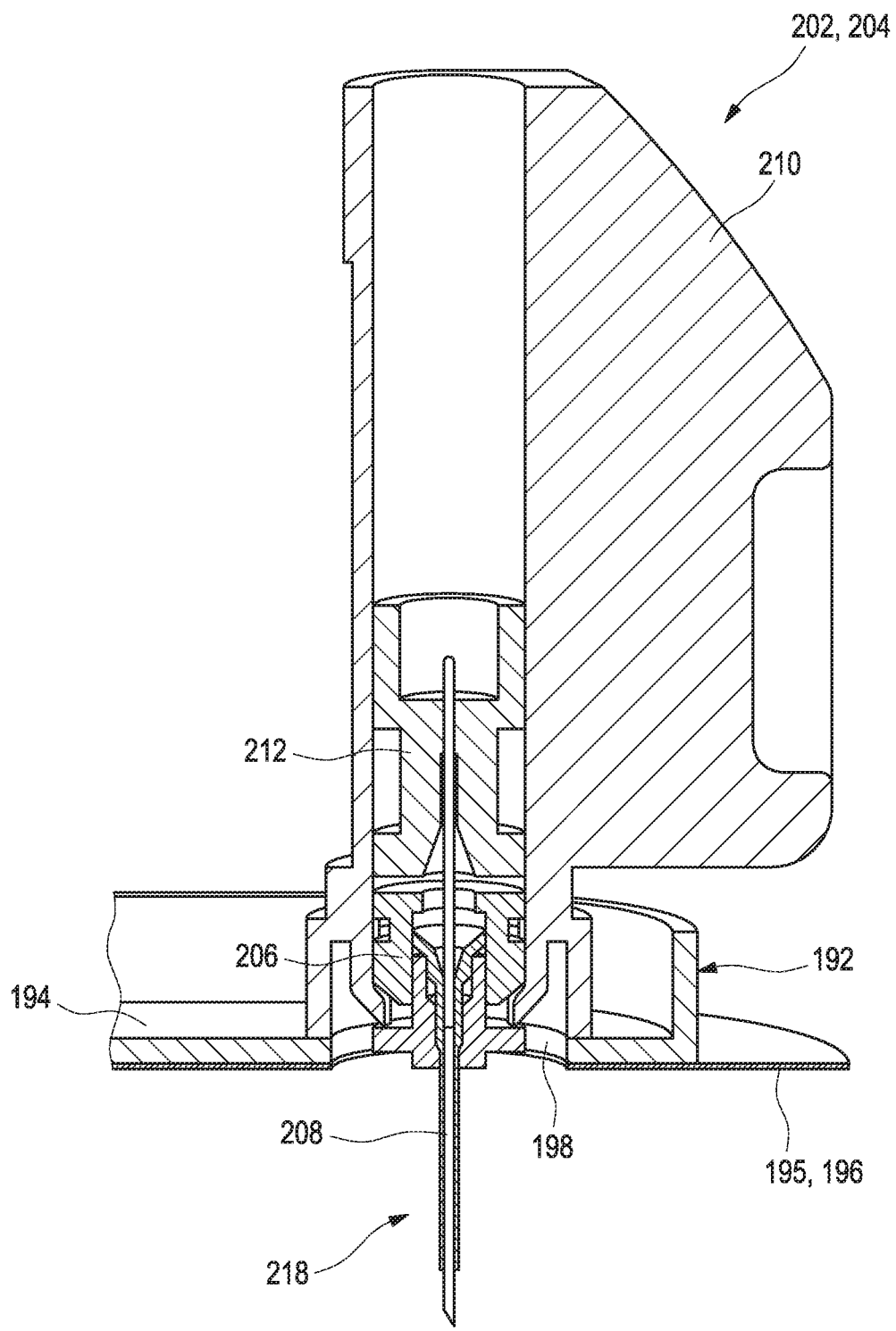

FIGS. 4A to 4C show an exemplary embodiment of a subsystem 202 in a disassembled view (FIG. 4A) and in different cross-sectional views (FIGS. 4B and 4C). The subsystem 202 is configured for being at least partially inserted into a host.

The subsystem 202 may specifically be a medication device 204 for providing at least one medication to the host. Exemplarily, the medication device 204 may comprise a cannula 206 and an insertion needle 208 which is removably receivable in the cannula 206. Therefore, the medication device 204 may comprise a needle housing 210 comprising the cannula 206 and the insertion needle 208. However, the cannula 206 may be replaced by additional or different subcutaneous elements such as a sensor and/or additional cannulas. The insertion needle 208 may have a mechanism attachment point 212 for attaching to an insertion mechanism. A portion of a mechanism may be inserted through a slot 214, specifically to a slot 214 of the needle housing 210, and may be used to press against the mechanism attachment point 212 to actuate the insertion needle 208.

In the cross-sectional view of the subsystem 202 as depicted in FIG. 4B the insertion needle 208 is shown before being inserted into the host. Specifically, the insertion needle 208 may be received in the needle housing 210. The insertion needle 208 may be in a retracted position 216.

In FIG. 4C the insertion needle 208 is shown in an extended position 218. Specifically, the insertion needle 208 may have been driven into the host. When the insertion needle 208 is withdrawn the cannula 206 may be left within the host.

Figure 5:
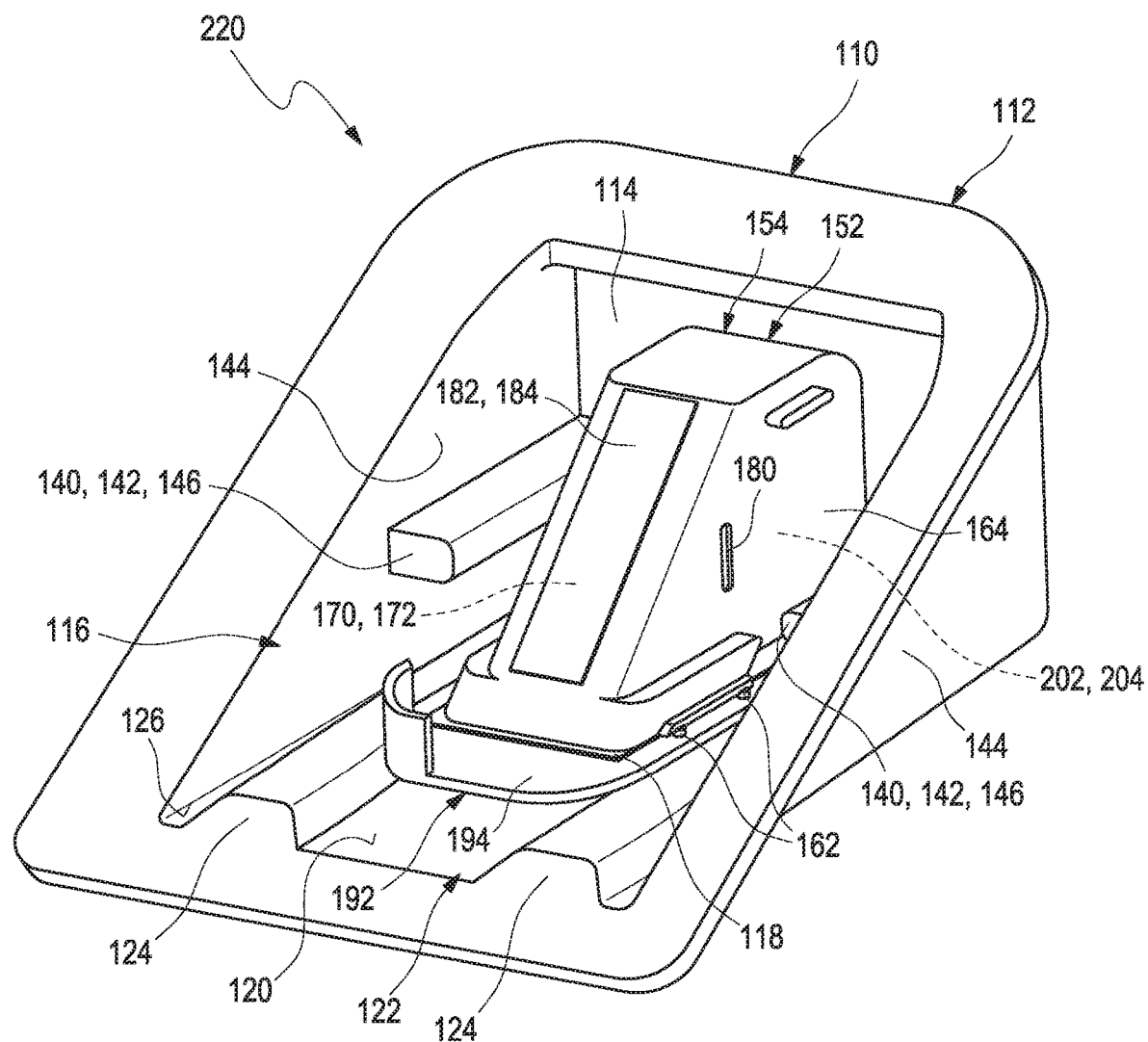
FIG. 5 shows an exemplary embodiment of a functional medical package in a perspective view.

FIG. 5 shows a functional medical package 220 in a perspective view. The medical package 220 comprises the disposable package 110, the sterile container 152 removable received inside the disposable package 110 and the subsystem 202 configured for being at least partially inserted into the host. The subsystem 202 is received in the sterile container 152.

The disposable package 110 corresponds at least in large parts to the disposable package 110 as illustrated in FIGS. 1A to 1D. The sterile container 152 corresponds at least on large parts to the sterile container 152 as depicted in FIGS. 2A to 3C. Thus, reference may be made to the descriptions of FIGS. 1A to 3C above. The subsystem 202 may exemplarily be or may comprise the medication device 204 as described in FIGS. 4A to 4C. However, other embodiments of the medication device 204 and/or of the subsystem 202 are feasible.

Figure 6:
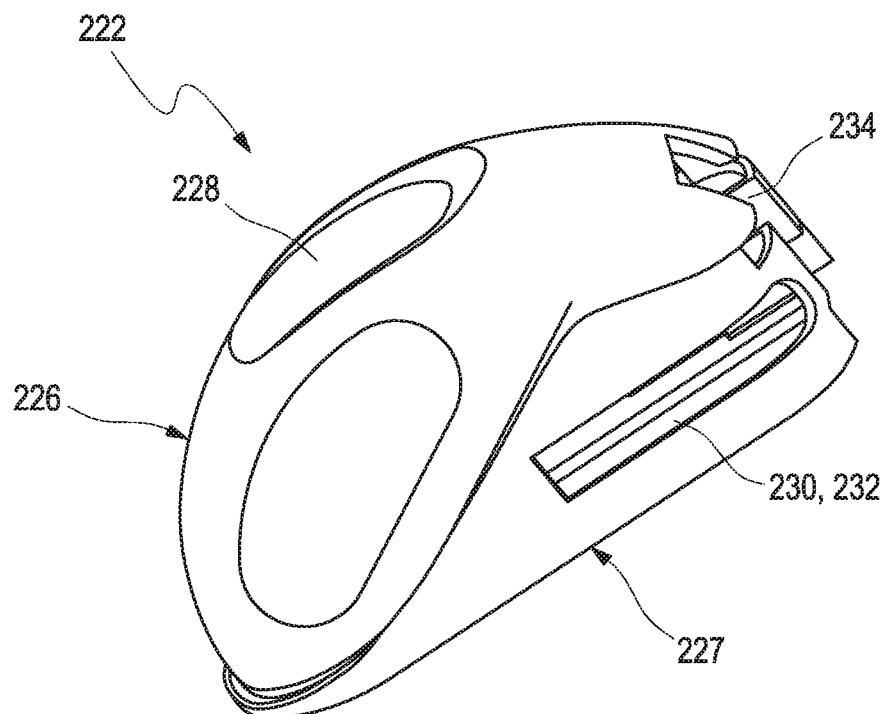
FIGS. 6A to 6C show an exemplary inserter in a perspective view (FIG. 6A), an exemplary medical device in a perspective view (FIG. 6B) and components of the medical device in a perspective view (FIG. 6C).
Figure 6:
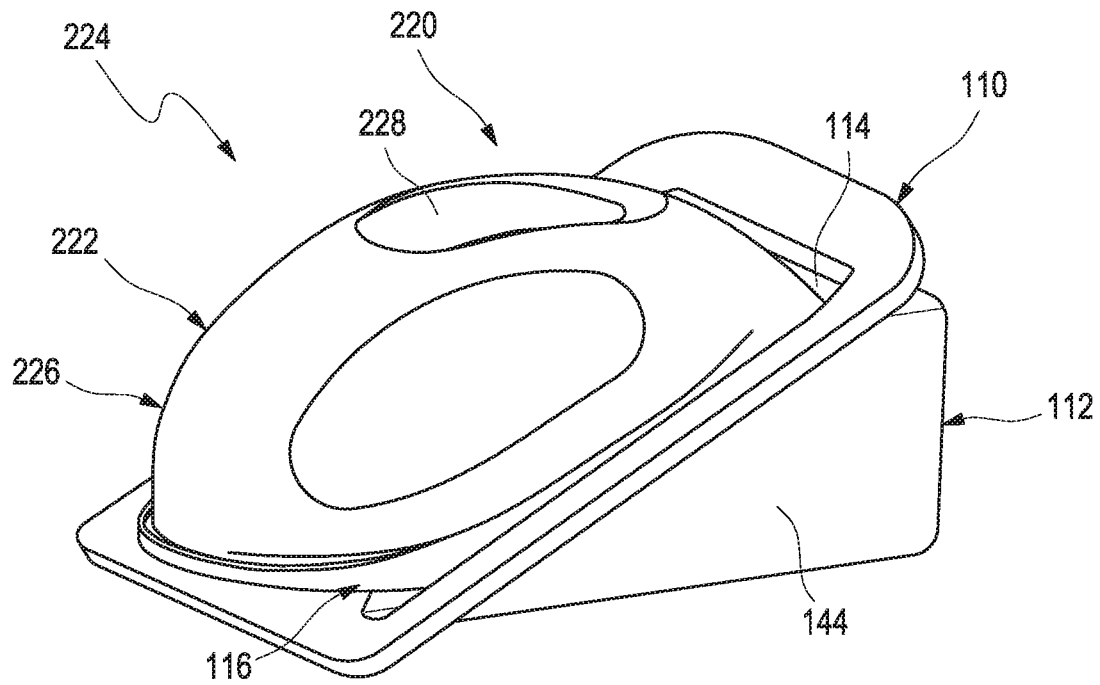
Figure 6:
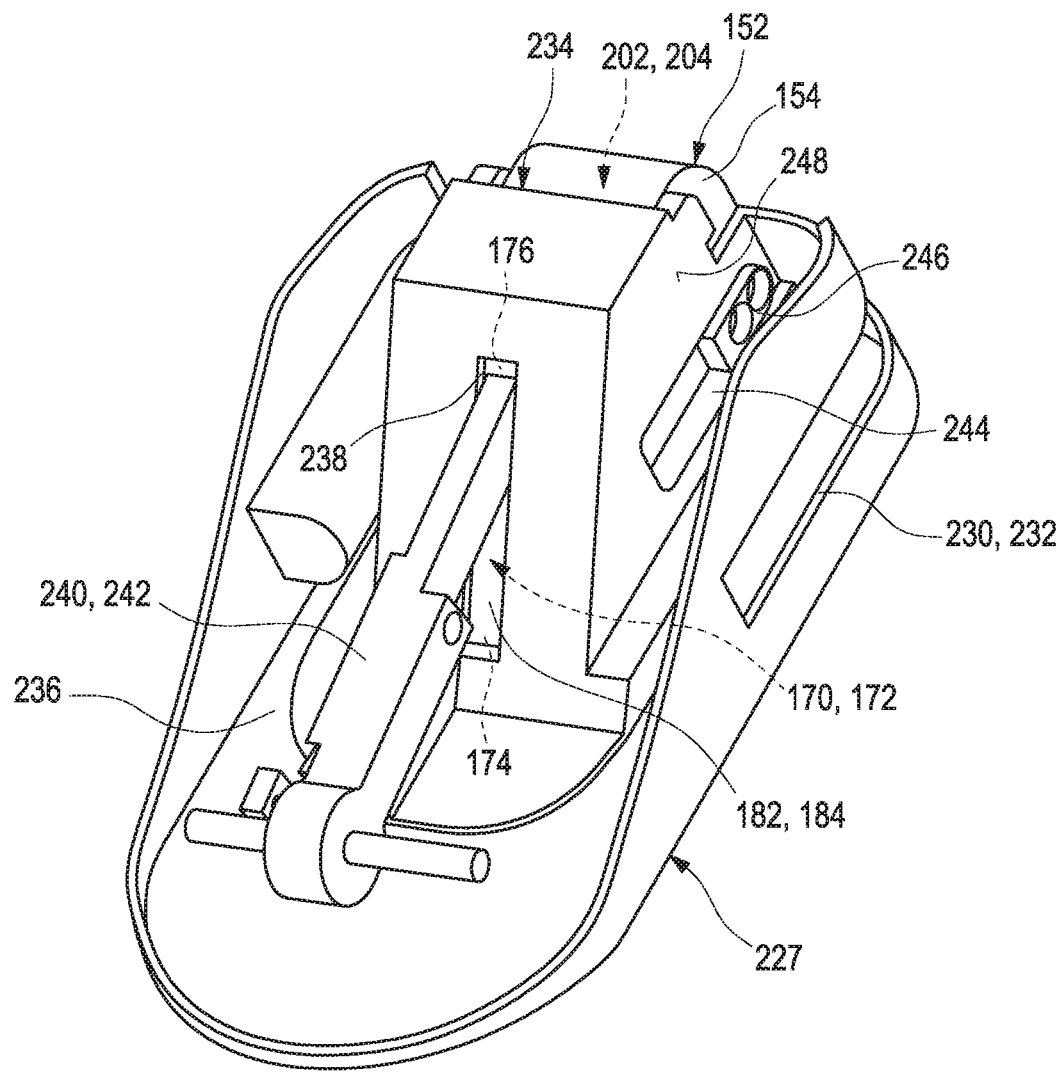

FIGS. 6A to 6C show an exemplary inserter 222 in a perspective view (FIG. 6A), an exemplary medical device 224 in a perspective view (FIG. 6B) and components of the medical device 224 in a perspective view (FIG. 6C).

The inserter 222 as illustrated in FIG. 6A may comprise at least one inserter cover 226. Further, the inserter 222 may comprise at least one button 228 to fire an insertion mechanism, specifically an insertion mechanism which is contained within the inserter cover 226. The inserter cover 226 may specifically cover an inserter base 227.

The inserter 222 may comprise at least one inserter guiding element 230. Exemplarily, the inserter guiding element 230 may be formed as grooves 232 within the inserter cover 226 of the inserter 222. Specifically, the inserter guiding element 230 may be complementary to the disposable package guiding element 140 as depicted within FIGS. 1A to 1D. Beyond this, the inserter 222 may comprise at least one inserter receptacle 234 configured for receiving the sterile container 152 as illustrated within FIGS. 2A to 2C.

FIG. 6B shows the medical device 224 for inserting the at least one subsystem 202 such as exemplarily illustrated within FIGS. 4A to 4C into the host. The medical device 224 comprises the at least one functional medical package 220. The functional medical package 220 may correspond at least in large parts to the functional medical package 220 as illustrated in FIG. 5. Thus, reference may be made to the description of FIG. 5 above. Further, the medical device 224 comprises the at least one inserter 222 as illustrated in FIG. 6A. The inserter 222 may be received into the functional medical package 220, specifically into the disposable package 110.

FIG. 6C specifically shows components of the medical device 224. The inserter cover 226 as illustrated in FIGS. 6A and 6B is removed and an interior space 236 of the inserter 222 is shown giving a view on the inserter base 227. The inserter base 227 may comprise the inserter receptacle 234 and the subsystem 202 may be received in the inserter receptacle 234. Specifically, the inserter receptacle 234 may comprise at least one inserter opening 238. The inserter opening 238 may be located above the drive opening 170 of the sterile container 152. Further, the inserter opening 238 may be identically shaped as the drive opening 170. At least one drive arm 240, specifically one lever 242, of the inserter 222 may be inserted in the inserter opening 238 of the inserter 222 and the drive opening 170. Thereby, the drive sealing element 182 may be opened. In FIG. 6C the drive arm 240 is illustrated in an upper position touching the upper end 176 of the drive opening 170. The drive arm 240 may put into a lower position touching the lower end 174 of the drive opening 170. Within this position, components of the subsystem 202 as described within FIGS. 4A to 4C may be at least partially inserted into the tissue of the host.

The inserter base 227 may further comprise one or more inserter base openings 244. The inserter base openings 244 may be located above the further sterile container receptacles 180 as illustrated within FIGS. 2A to 3C. The inserter 222 may comprise at least one, preferably two, clamping elements 246 configured to establish a form-fit connection between the inserter 222 and the sterile container 152. Therefore, the clamping elements 246 may be fixed on an outer surface 248 of the inserter base 227 facing the inserter cover 226 and may further be located next to the inserter base openings 244. Specifically, the clamping element 246 may engage in the further sterile container receptacle 180 via the inserter base openings 244.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

LIST OF REFERENCE NUMBERS 110 disposable package
112 disposable package housing
114 interior volume
116 disposable package opening
118 liner sealing
120 disposable package supporting surface
122 receptacle
124 rack
126 surface
128 upper surface
130 lower surface
132 adhesive surface
134 end
136 passage opening
138 outer surface
140 disposable package guiding element
142 first disposable package guiding element
144 side wall
146 guide rail
148 second disposable package guiding element
150 contour
152 sterile container
154 sterile container housing
156 interior space
158 sterile container guiding element
160 guide rail
162 retaining pin
164 sterile container side wall
166 direction of extension
168 insertion exit opening
170 drive opening
172 slit
174 lower end
176 upper end
178 sterile container receptacle
180 further sterile container recepatacle
182 drive sealing element
184 plastic foil
186 rim
188 attachment component
190 sealing surface
192 body mount
194 body mount base
195 adhesive surface
196 plaster
198 body mount housing
200 gap
202 subsystem
204 medication device
206 cannula
208 insertion needle
210 needle housing
212 mechanism attachment point
214 slot
216 retracted position
218 extended position
220 functional medical package
222 inserter
224 medical device
226 inserter cover
227 inserter base
228 button
230 inserter guiding element
232 groove
234 inserter receptacle
236 interior space
238 inserter opening
240 drive arm
242 lever
244 inserter base opening
246 clamping element
248 outer surface

What is claimed is:

1. A functional medical package, comprising:
a disposable package;
a sterile container removably received in the disposable package; and
a subsystem received in the sterile container, the subsystem configured to be at least partially inserted into a host;
the sterile container having an insertion exit opening for the subsystem;
a liner closing the insertion exit opening, wherein the liner is attached to the disposable package and the liner automatically peels off the insertion exit opening when the sterile container is removed from the disposable package; and
wherein the disposable package defines a liner opening and the liner includes a first portion that seals the insertion exit opening and a second portion that extends through the liner opening and is attached to an outer surface of the disposable package.

2. The functional medical package according to claim 1, wherein the subsystem is selected from the group consisting of: an analyte sensor for detecting at least one analyte in a body tissue and a medication device for providing at least one medication to the host.

3. The functional medical package according to claim 2, wherein the subsystem is a medication device and the medication device comprises a cannula and an insertion needle which is removably receivable in the cannula.

4. The functional medical package according to claim 1, wherein the disposable package comprises a second disposable package opening through which the sterile container is removable from the disposable package.

5. The functional medical package according to claim 4, wherein the second disposable package opening is sealed by at least one sealing element.

6. The functional medical package according to claim 1, further comprising a body mount configured for attachment to a skin of the host.

7. The functional medical package according to claim 6, wherein the sterile container is attached to the body mount.

8. The functional medical package according to claim 6, wherein the sterile container and the body mount are removable from the disposable package as a unit.

9. A medical device for inserting at least one subsystem into a host, the medical device comprising:
- a functional medical package according to claim 1; and
- an inserter configured for inserting the subsystem into the host.

10. A functional medical package, comprising:
- a disposable package;
- a sterile container removably received in the disposable package; and
- a subsystem received in the sterile container, the subsystem configured to be at least partially inserted into a host;
- the sterile container having an insertion exit opening for the subsystem;
- a liner closing the insertion exit opening, wherein the liner is attached to the disposable package and the liner automatically peels off the insertion exit opening when the sterile container is removed from the disposable package; and
- wherein the sterile container comprises a sterile container housing having the insertion exit opening, and wherein the sterile container further comprises a drive opening for enabling an actuator of an inserter to enter the sterile container and to engage with the subsystem for insertion into the host.

11. The functional medical package according to claim 10, wherein the drive opening is sealed by a drive seal.

12. The functional medical package according to claim 11, wherein the drive seal is configured to be cut open.

13. The functional medical package according to claim 12, wherein the drive seal is configured to be cut open by at least one drive arm of the inserter and/or by a cutting mechanism of the inserter.

* * * * *